United States Patent [19]

Carron et al.

[11] 4,377,559
[45] Mar. 22, 1983

[54] NEW METHOD OF DISPOSING OF THE RESIDUE FROM THE PRODUCTION OF DIAKLYL PHOSPHOROCHLORIDOTHIONATE

[75] Inventors: Mark S. Carron, Spring Valley; Carl C. Greco, Garnerville; Lester P. VanBrocklin, Thiells; Francis A. Via, Yorktown Heights, all of N.Y.

[73] Assignee: Stauffer Chemical Company, Westport, Conn.

[21] Appl. No.: 296,109

[22] Filed: Aug. 26, 1981

[51] Int. Cl.$^3$ .............................................. C01B 25/16
[52] U.S. Cl. .................................... 423/317; 423/540; 423/563; 423/567 R
[58] Field of Search ................... 423/317, 563, 567 R, 423/540

[56] References Cited

FOREIGN PATENT DOCUMENTS 2617812  4/1976  Fed. Rep. of Germany .

*Primary Examiner*—O. R. Vertiz
*Assistant Examiner*—Gregory A. Heller
*Attorney, Agent, or Firm*—Vivienne T. White

[57] ABSTRACT

The invention is a method of treating the distillation residue from the production of phosphorochloridothionates which comprises draining the residue into agitated cold water to form a slurry and contacting the slurry with chlorine gas in a hydrolyzing zone to decompose the residue and produce decomposition gases in controllable amounts having a decreased sulfur content.

The novel method would reduce the amount of sulfur in the decomposition gas and make possible the use of less costly abatement facilities.

7 Claims, No Drawings

NEW METHOD OF DISPOSING OF THE RESIDUE FROM THE PRODUCTION OF DIAKLYL PHOSPHOROCHLORIDOTHIONATE

BACKGROUND OF THE INVENTION

1. Field of the Invention

The invention in general pertains to a method of disposing of the residue from the production of dialkyl and diaryl phosphorochloridothionate in an environmentally safe manner.

2. Prior Art

The distillation residue formed when phosphorochloridothionates are produced, as for instance, by the method disclosed in U.S. Pat. No. 3,089,890 incorporated herein by reference, is essentially comprised of a plastic mass of undissolved sulfur, dissolved organophosphorous compounds and other undissolved compounds. The distillation residue, which is generally disposed of by hydrolysis on a batch basis, has a highly offensive odor and is, in addition, thermally unstable.

When phosphorochloridothionate is prepared on a batch basis, the distillation residue resulting therefrom is disposed of by draining it into cold agitated water in a hydrolyzing zone, and heating the mixture slowly to a temperature of from 90°–120° C. By this process, the residue is decomposed into gases. However, the decomposition gases are produced at very uneven rates. During the peak rates of gas production, the odorous decomposition gases produced require the use of large volumes of air and fuel to prevent the odorous gases from escaping air swept hydrolyzers and abatement facilities into the atmosphere. These gases can cause severe odor problems. The decomposition gases resulting from the hydrolysis of the residue from the production of dialkyl phosphorochloridothionate can comprise HCl, ROH RSH, $H_2S$, RCl, $CS_2$ and $RS_xR$, where R in an alkyl or aryl radical. The decomposition gases are generally burnt in an incinerator at from about 750° C.–800° C.

These gases contain from about 30 to 50 weight percent sulfur, and therefore, require large abatement facilities to effectively prevent the escape of polluting gases such as $SO_2$, $H_2S$, RSH, etc. to the atmosphere. The use of large abatement facilities to adequately eliminate such pollution require high fuel consumption and concomitant high costs.

A prior art method for treating the residue from the production of dialkyl thiophosphoric acid chloride is disclosed in German patent application No. P 2617812, filed Apr. 23, 1976. The method comprises placing the residue in alkalyzed water having a temperature of about −10° C. to about 50° C. and a pH of at least 10 in the resulting mixture, and contacting the aqueous phase and/or solid phases of the mixture formed therein with nitric acid at an elevated temperature and at a pH of below 3, convert the residue into fertilizer and/or crystalline sulfur.

Also, there is disclosed in U.S. patent application Ser. No. 78,640, filed Sept. 26, 1979, a process of treating distillate residue from phosphorochloridothionate production by introducing the residue into agitated water to form a pumpable and storeable slurry which is then hydrolyzed in controllable amounts.

It is an object of the present invention to provide a method of hydrolyzing the distillation residue whereby the sulfur content of the evolved waste gases is substantially reduced. A further object of the invention is to provide a method of hydrolyzing the distillation residue in controllable amounts which would dispense with the need for costly abatement facilities.

SUMMARY OF THE INVENTION

The invention is a method for treating the residue from the production of phosphorochloridothionates comprising the steps of: (a) contacting the residue with water and a chlorinating agent to form a chlorinated slurry wherein elemental sulfur is precipitated in the liquid phase; (b) hydrolyzing the chlorinated slurry in controllable amounts to produce decomposition gases having a decreased sulfur content. The invention preferably contemplates first introducing the residue into agitated water to form a slurry prior to contacting the residue with chlorine and incinerating the decomposition gases after hydrolyzing the chlorinated slurry whereupon $SO_2$ is produced in significantly decreased amounts.

DETAILED DESCRIPTION OF THE INVENTION

The invention relates to a method of treating the residue from the production of dialkyl phosphorochloridothionates to eliminate the need for costly abatement facilities by decreasing the volume of decomposition gases produced and more particularly decreasing the amount of $SO_2$ produced during the incineration after hydrolysis of the residue. In the novel method disclosed herein, the sulfur content of the evolved waste gases is significantly reduced by precipitating the sulfur in the liquid. This shifting of a significant amount of the sulfur content from vapor to liquid phase is very advantageous to the pollution control operations since removal of sulfur from the vapor phase is a difficult and expensive operation while disposal of liquid sulfur is a relatively easier and cheaper operation.

The principal reactions in producing phosphorochloridothionates are:

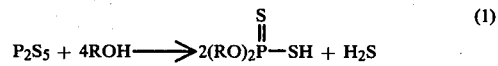

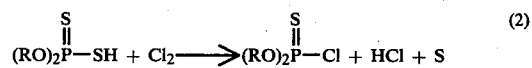

wherein R is a lower alkyl of from 1–8 carbon atoms. The extent to which chlorination (reaction 2) side reactions occur and form by-products varies, however most of the by-products of dialkyl phosphorodithionic acid production (reaction 1) have been characterized. The products of reaction (1) can comprise, for instance:

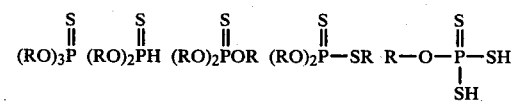

In the prior art process, the hydrolysis of the residue produces gases mainly consisting of $H_2S$, HCl, ROH, RCl, RSH, $CS_2$, $RS_xR$, and the like, R being the same as above, and a liquid which contains about 30–50 weight percent sulfur in addition to phosphoric acid as $H_3PO_4$.

In the novel method of this invention, the residue remaining after the distillate separation of the phosphorochloridothionate product is advantageously decomposed such that $H_2S$ in a significantly decreased amount is produced, which when incinerated produces a correspondingly decreased amount of $SO_2$. Decreasing the amounts of $SO_2$, after incineration of the residue, allows for the utilization of less costly $SO_2$ abatement method such as, for instance, the Claus process for substantially complete $SO_2$ abatement.

In the Claus abatement process, the $H_2S$ which is initially produced in equation (1) is combined and reacted with the $SO_2$ resulting from the incineration of the residue from equation (2). Due to the novel process disclosed herein, by chlorinating the residue prior to decomposition, the ratio of the $H_2S$ produced as a result of equation (1) relative to the $SO_2$ produced by the decomposition of the distillation residue from equation (2) is increased. This allows for the complete combustion of the sulfur dioxide and hydrogen sulfide in the Claus process as examplified by the following reaction:

$$2H_2S + SO_2 \rightarrow 3S + 2H_2O$$

In the practice of the invention, the residue from a batch or continuous process for producing phosphorochloridothionates is drained into agitated cold water and the resulting mixture or slurry, which is comprised of water, organic and elemental sulfur particles, is then chlorinated by contacting with a chlorinating agent, such as chlorine gas, at a temperature of from about 10° C. to about 150° C. and preferably a temperature of from about 40° C. to about 60° C.

The slurry formed before chlorination by draining the residue into cold agitated water is both pumpable and storable and therefore can be decomposed by hydrolysis in controllable amounts by controlling the feed rate to the hydrolyzer, thereby providing a means for decreasing the volume of decomposition gases produced.

Chlorination of the slurry can be accomplished prior to batch hydrolysis or in a continuous manner during continuous controlled hydrolysis of the residue.

In accordance with the invention, a chlorinating agent may be added continuously to a hydrolyzing zone with the continuous addition of the residue slurry. The residue slurry can also be initially chlorinated and, thereafter, the chlorinated slurry can be continuously introduced into the hydrolyzing zone in controllable amounts.

The amount of chlorine added to the slurry in accordance with the invention can be either stoichiometric or an excess amount, based on one mole of chlorine per mole of phosphorus in the residue. The chlorination of the slurry can be accomplished by any of the known methods such as by addition of gaseous chlorine, or liquid chlorination (oxidative) agents, and preferably by addition of chlorine (gas).

Chlorinating agents, such as chlorine, sulfur dichloride, sulfur monochloride, sulfuryl chloride and the like may be used but the preferred chlorinating agent for use is chlorine.

After chlorination of the residue slurry, the chlorinated residue slurry is hydrolyzed at a temperature of from about 80° C. to about 150° C. and preferably from about 100° C. to about 105° C.

The hydrolysis step converts the residue slurry to a phosphoric acid solution and a sulfur layer. The $H_2S$ and other sulfides in the evolved waste gases are dramatically reduced in the practice of the invention. Due to the reduction in the sulfur content of the evolved waste gases, the incineration of the gases produces a significantly lesser amount of $SO_2$ which allows for the scaling down of abatement facilities or their elimination in favor of a more energy effective method of abatement such as the Claus process.

EXAMPLE

Four samples of residue from the production of dimethyl phosphorochloridothionate (DMPCT) production were chlorinated by placing each sample in a reactor flask and adding thereto an amount of acidic wash water (typical process wash water comprises an aqueous solution of about 7.4% $H_3PO_4$ and 6.5% HCl). The reactants were then heated with stirring to 60° C. Amounts of gaseous chlorine were added to the reaction over a 2 hour period. Table 1 below gives the amounts of the reactants added to each sample of the residue.

TABLE 1

| | Residue Sample (gm) | Wash Water (gm) | Chlorine Added (gm) |
|---|---|---|---|
| 1 | 38 | 78 | 10 |
| 2 | 42 | 78 | 7.8* |
| 3 | 38.5 | 78 | 15** |
| 4 | 28.4 | 51.3 | — |

*30% less than stoichiometry
**50% over stoichiometry

During the chlorine addition, the reaction temperature was maintained between 60° C. and 80° C. Upon completion of the chlorine addition, the reaction mixture was heated to 100° C. whereupon water was distilled off. As the water distilled off the temperature rose to 110° C. over a 6 hour period. The vent gases were collected in traps. After completion of the hydrolysis step, the reaction mixture was cooled to room temperature and the layers ($H_2O$, $H_3PO_4$ and sulfur) separated. The results obtained showed the effect of chlorination on the hydrolyzer gas composition as well as the effect of chlorine stoichiometry. The results are shown in the following table.

TABLE 2

| | Sample 1 (Stoichiometric) | Sample 2 30% Cl Deficinecy | Sample 3 50% Cl Excess | Sample 4 No Cl |
|---|---|---|---|---|
| % $H_2S$ in Volatiles | 4% | 4% | 1% | 26% |
| % Methyl Sulfides* in Volatiles | 0% | 21% | 8% | 7% |
| Ratio of Sulfur to Starting Residue Obtained | .56 | .43 | .56 | .46 |
| Ratio of Exit Gases to Residue | .34 | .36 | .68 | .33 |
| Sulfur Quality | 99% | 89% | 91% | 99% |

*$CH_3S_xCH_3$ where x = 1, 2, or 3

The process of the invention reduces the sulfur content of the hydrolyzer gases by a factor of at least 7. The residue samples utilized in the Examples given above were small portions of the overall residue as obtained without first forming a residue slurry. In a Plant scale treatment of the residue (especially a continuous process) in accordance with the above invention, it would be necessary to first form the residue slurry so that controllable amounts of the residue could be easily obtained for hydrolysis. Advantageously a very high-purity sulfur residue is obtained utilizing the process of the invention.

What is claimed is:

1. A method of treating the residue from the production of phosphorochloridothionates comprising the steps of:
   (a) contacting the residue with water and a chlorinating agent in an amount sufficient to form a chlorinated slurry wherein the amount of sulfur precipitated in the liquid phase is increased;
   (b) hydrolyzing the chlorinated slurry in controllable amounts to produce decomposition gases having a decreased sulfur content, and other by-products comprising sulfur and phosphoric acid.

2. The method of claim 1 further comprising introducing the residue into sufficient agitated water to form a pumpable slurry.

3. The method of claim 1 or 2 further comprising incinerating the decomposition gases whereby $SO_2$ is produced in significantly decreased amounts.

4. The method of claim 1 wherein the chlorinating agent is chlorine gas.

5. The method of claim 4 or claim 1 wherein the amount of chlorinating agent utilized is stoichiometric with respect to the amount of phosphorous in the residue.

6. The method of claim 1 wherein the slurry is contacted with the chlorinating agent at a temperature of from about 40° C. to about 60° C.

7. The method of claim 1 wherein the chlorinated residue is hydrolyzed at a temperature of from about 80° C. to about 150° C.

* * * * *